United States Patent [19]
Collini et al.

[11] Patent Number: 5,932,743
[45] Date of Patent: Aug. 3, 1999

[54] METHODS FOR THE SOLID PHASE SYNTHESIS OF SUBSTITUTED INDOLE COMPOUNDS

[75] Inventors: Michael D. Collini, Clifton Heights, Pa.; John W. Ellingboe, Ridgewood, N.J.

[73] Assignee: American Home Products Corporation, Madison, N.J.

[21] Appl. No.: 09/124,348

[22] Filed: Jul. 29, 1998

Related U.S. Application Data

[60] Provisional application No. 60/056,229, Aug. 21, 1997.
[51] Int. Cl.[6] ...................... C07D 209/08; C07D 209/10; C07D 209/12; C07D 209/14
[52] U.S. Cl. ...................... 548/508; 548/490; 548/491; 548/504; 548/506; 548/507; 548/509; 548/510; 548/511
[58] Field of Search ...................... 514/415, 418; 548/483, 484, 491, 508, 490, 504, 510

[56] References Cited

PUBLICATIONS

Hermkens, et al., Tetrahedron Lett., 52, 4527–4554 (1996).
Comprehensive Heterocyclic Chem., 4, 370–376; Pergamon Press, Oxford (1984).
Borman, S., Chemical & Engineering News, 75(8) 43–62 (1997).
Arcadi A., et al., Tetrahedron Lett., 33, 3915–3918 (1992).
Hutchins, S.M. et al., Tetrahedron Lett., 37, 4867–4872 (1996).
Fagnola et al., Tetrahedron Lett. 38 (13) 2307–2310 (1997).

*Primary Examiner*—Johann Richter
*Assistant Examiner*—Jane C. Oswecki
*Attorney, Agent, or Firm*—Rebecca R. Barrett

[57] ABSTRACT

The present invention relates to novel substituted indole compounds of formula (I)

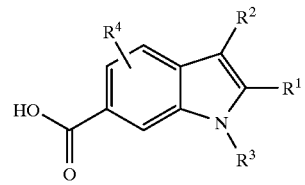

(I)

having pharmacological activity, to processes for their preparation, to solid phase methods for preparing libraries of the compounds, to utilizing libraries of the compounds for drug discovery, and to pharmaceutical compositions thereof.

22 Claims, No Drawings

METHODS FOR THE SOLID PHASE SYNTHESIS OF SUBSTITUTED INDOLE COMPOUNDS

This application claims the benefit of U.S. Provisional application No. 60/056,229, filed Aug. 21, 1997.

FIELD OF THE INVENTION

The present invention relates to novel substituted indole compounds having pharmacological activity, to processes for their preparation, to combinatorial and solid phase methods for preparing libraries of the compounds, to utilizing libraries of the compounds for drug discovery, and to pharmaceutical compositions thereof.

BACKGROUND OF THE INVENTION

The solid phase synthesis of non-peptidic small organic molecules is a rapidly evolving area of research with applications in the preparation of combinatorial libraries. While the solid phase synthesis of peptides is an established, the solid phase synthesis of non-peptidic small organic molecules is still evolving (Hermkens, P. H. H.; Ottenheijm, H. C. J.; Rees, D. Tetrahedron 1996, 52, 4527–4554). In particular, methods for the solid phase synthesis of heterocyclic ring systems of importance to drug discovery is an active area of research.

Indoles are an important class of molecules with physiological significance and pharmaceutical utility. In synthetic and natural product chemistry, the indole ring system has broad pharmacological activity (Sundberg, R. J. in Comprehensive Medicinal Chemistry, Vol. 4, pp. 370–376; Pergamon Press: Oxford, 1984). An example of the physiological significance of the indole ring system is serotonin, which is of overwhelming importance for normal psychological function. Two important pharmaceutical areas are anti-inflammatory drugs such as indomethacin and drugs acting on the central nervous system. Indoles have also found use in other therapeutic areas.

Combinatorial chemistry is becoming an important tool for drug discovery and lead optimization (Borman, S. Chemical and Engineering News 1997, 75 (8), 43–62). A combinatorial synthesis requires that at least two components of the product molecules be independently variable, so that all of the combinations of these components can be prepared. A synthesis with three independently variable components is preferable since greater diversity in structure can be produced in the resultant library. Thus, to prepare a combinatorial library of indoles with a high degree of potential diversity and wide utility for drug discovery using solid phase techniques, it is important to identify an indole synthesis in which three components can be independently varied. The solution phase synthesis of indoles reported by Arcadi and Cacchi (Arcadi, A.; Cacchi, S.; Marinelli, F. Tetrahedron Lett. 1992, 33, 3915–3918) incorporates two components in an independent fashion through palladium-catalyzed processes. The indoles prepared by this route can then be alkylated on nitrogen to incorporate a third component. By adapting the solution phase synthesis to a solid-supported synthesis, it is possible to prepare combinatorial libraries of indoles at room temperature under neutral or mildly basic conditions and thus there are few limitations to the solid support and linker used.

A solid phase synthesis of indoles requiring elevated temperatures and acidic conditions has been reported (Hutchins, S. M.; Chapman, K. T. Tetrahedron Lett. 1996, 37, 4869–4872). The solid-phase Fisher indole synthesis requires elevated temperatures and acidic conditions which limit the types of linkers and solid supports that can be used for the synthesis. Fagnola et al., Tetrahedron Letters 1997, 38, (13), 2307–2310, disclose a solid phase synthesis of 2-substituted indoles using the palladium-catalysed coupling of alkynes with N-acetyl iodoaniline derivatives. Only one variable group is introduced in the synthesis so it is not ideal for the preparation of combinatorial libraries.

Multiple compounds can be prepared simultaneously by the solid phase process. The simultaneous solid phase synthesis of a library of 2,3-disubstituted indoles of the present invention is not known. The preparation of libraries of compounds of the present invention is useful because it provides rapid structural variation and structure-activity information.

The libraries of substituted indoles synthesized according to the present invention are useful for drug discovery. For example, screening one of the indole libraries in an estrogen receptor assay identified compounds with estrogen agonist activity. Estrogen agonists are useful as post-menopausal therapeutics for the prevention and treatment of osteoporosis, atherosclerosis, and Alzheimer's disease.

BRIEF DESCRIPTION OF THE INVENTION

Accordingly, the present invention discloses a solid phase synthesis process for producing compounds represented by the formula (I):

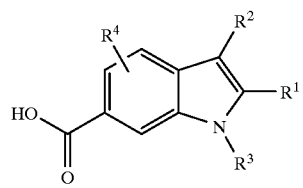

wherein:

$R^1$ is straight chain alkyl of 1 to 6 carbon atoms, branched chain alkyl of 3 to 7 carbon atoms, cycloalkyl of 3 to 7 carbon atoms, phenyl, phenylalkyl of 7 to 12 carbon atoms, or straight chain alkyl of 1 to 6 carbon atoms substituted with

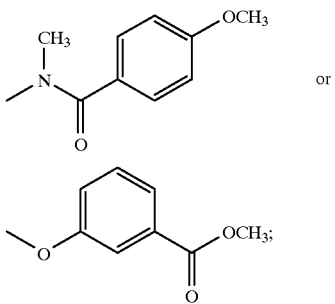

$R^2$ is straight chain alkenyl of 2 to 6 carbon atoms, branched chain alkenyl of 3 to 7 carbon atoms, cycloalkenyl of 3 to 7 carbon atoms, phenyl,

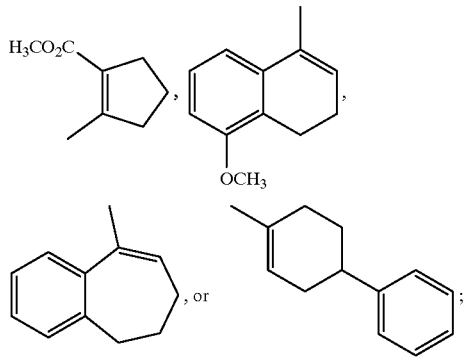

$R^3$ is hydrogen, straight chain alkyl of 1 to 6 carbon atoms optionally substituted with one $COOR^5$, branched chain alkyl of 3 to 7 carbon atoms, cycloalkyl of 3 to 7 carbon atoms, or phenylalkyl of 7 to 12 carbon atoms optionally substituted with one $COOR^5$, phenyl, or acyl group;

$R^4$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

$R^5$ is hydrogen, straight chain alkyl of 1 to 6 carbon atoms, or phenylalkyl of 7 to 12 carbon atoms;

and all crystalline forms and the pharmaceutically acceptable salts thereof, the enantiomers thereof, the racemic mixtures thereof, and the diastereomeric mixtures thereof which comprises the steps of:

a) attaching a 3-amino-4-iodo-benzoic acid of the formula

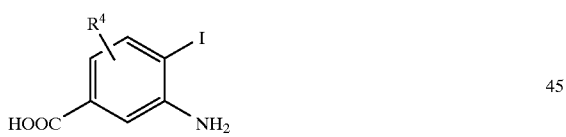

or an alkaline metal salt thereof to a solid support P to produce a compound of formula (1)

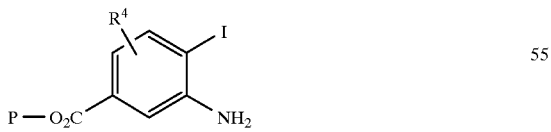
(1)

wherein $R^4$ is as defined above and P is preferably a polystyrene resin crosslinked with divinylbenzene and functionalized with a linker such as a hydroxymethylphenoxy group, and more preferably Wang's resin as described below; and b) reacting said compound of formula (1) with a terminal alkyne of formula (2),

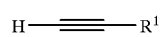
(2)

wherein $R^1$ is as defined above, in the presence of a palladium catalyst, copper(I) iodide, and amine base in a polar aprotic solvent at ambient temperature to produce a compound of formula (3)

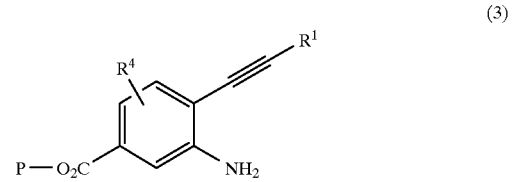
(3)

wherein $R^1$, $R^4$, and P are as defined above; and c) reacting said compound of formula (3) with trifluoroacetic anhydride and an amine base in dichloromethane to produce a compound of formula (4)

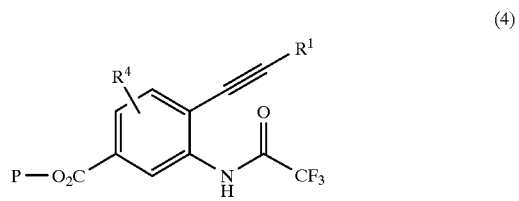
(4)

wherein $R^1$, $R^4$, and P are as defined above; and d) reacting said compound of formula (4) with a vinyl trifluoromethanesulfonate of formula (5)

TfO—$R^2$ (5)

wherein $R^2$ is as defined above, in the presence of a palladium catalyst and potassium carbonate in a polar aprotic solvent to produce a compound of formula (6)

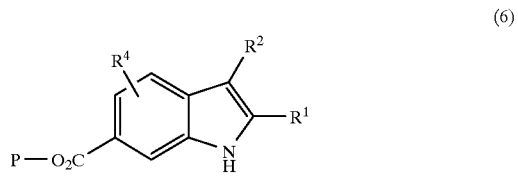
(6)

wherein $R^1$, $R^2$, $R^4$, and P are as defined above; and e) reacting said compound of formula (6) with an alkylating agent $R^3X$, where X is a suitable leaving group known to those skilled in the art, in the presence of sodium hydride in a polar aprotic solvent to produce a compound of formula (7)

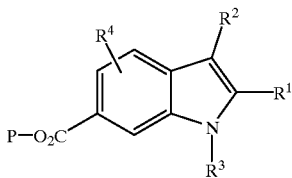

(7)

wherein $R^1$, $R^2$, $R^3$, $R^4$, and P are as defined above; and f) reacting said compound of formula (7) with a cleaving reagent such as trifluoroacetic acid to produce a compound of formula (I)

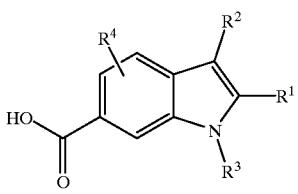

(I)

wherein $R^1$, $R^2$, $R^3$, and $R^4$ are as defined above.

The term "phenylalkyl of 7 to 12 carbon atoms" which appears in the definitions of $R^1$–$R^5$ refers to the group "phenyl-$(CH_2)_n$—" where n is 1 to 6.

The most preferred aspects of the present invention are the solid phase synthesis processes for producing:

2-butyl-3-(2-methoxycarbonyl-cyclopent-1-enyl)-1H-indole-6-carboxylic acid or a pharmaceutically acceptable salt thereof;

2-butyl-3-(2-methoxycarbonyl-cyclopent-1-enyl)-1-methyl-1H-indole-6-carboxylic acid or a pharmaceutically acceptable salt thereof;

2-butyl-1-ethoxycarbonylmethyl-3-(2-methoxycarbonyl-cyclopent-1-enyl)-1H-indole-6 carboxylic acid or a pharmaceutically acceptable salt thereof;

2-butyl-1-carboxymethyl-3-(2-methoxycarbonyl-cyclopent-1-enyl)-1H-indole-6-carboxylic acid or a pharmaceutically acceptable salt thereof;

2-butyl-1-(4-methoxycarbonyl-benzyl)-3-(2-methoxycarbonyl-cyclopent-1-enyl)-1H-indole-6-carboxylic acid or a pharmaceutically acceptable salt thereof;

1-biphenyl-4-ylmethyl-2-butyl-3-(2-methoxycarbonyl-cyclopent-1-enyl)-1H-indole-6-carboxylic acid or a pharmaceutically acceptable salt thereof;

2-cyclopentyl-3-(2-methoxycarbonyl-cyclopent-1-enyl)-1H-indole-6-carboxylic acid or a pharmaceutically acceptable salt thereof;

2-cyclopentyl-3-(2-methoxycarbonyl-cyclopent-1-enyl)-1-methyl-1H-indole-6-carboxylic acid or a pharmaceutically acceptable salt thereof;

2-cyclopentyl-1-ethoxycarbonylmethyl-3-(2-methoxycarbonyl-cyclopent-1-enyl)-1H-indole-6-carboxylic acid or a pharmaceutically acceptable salt thereof;

1-carboxymethyl-2-cyclopentyl-3-(2-methoxycarbonyl-cyclopent-1-enyl)-1H-indole-6-carboxylic acid or a pharmaceutically acceptable salt thereof;

2-cyclopentyl-1-(4-methoxycarbonyl-benzyl)-3-(2-methoxycarbonyl-cyclopent-1-enyl)-1H-indole-6-carboxylic acid or a pharmaceutically acceptable salt thereof;

1-biphenyl-4-ylmethyl-2-cyclopentyl-3-(2-methoxycarbonyl-cyclopent-1-enyl)-1H-indole-6-carboxylic acid or a pharmaceutically acceptable salt thereof;

3-(2-methoxycarbonyl-cyclopent-1-enyl)-2-phenyl-1H-indole-6-carboxylic acid or a pharmaceutically acceptable salt thereof;

3-(2-methoxycarbonyl-cyclopent-1-enyl)-1-methyl-2-phenyl-1H-indole-6-carboxylic acid or a pharmaceutically acceptable salt thereof;

1-ethoxycarbonylmethyl-3-(2-methoxycarbonyl-cyclopent-1-enyl)-2-phenyl-1H-indole-6-carboxylic acid or a pharmaceutically acceptable salt thereof;

1-carboxymethyl-3-(2-methoxycarbonyl-cyclopent-1-enyl)-2-phenyl-1H-indole-6-carboxylic acid or a pharmaceutically acceptable salt thereof;

1-(4-methoxycarbonyl-benzyl)-3-(2-methoxycarbonyl-cyclopent-1-enyl)-2-phenyl-1H-indole-6-carboxylic acid or a pharmaceutically acceptable salt thereof;

1-biphenyl-4-ylmethyl-3-(2-methoxycarbonyl-cyclopent-1-enyl)-2-phenyl-1H-indole-6-carboxylic acid or a pharmaceutically acceptable salt thereof;

3-(2-methoxycarbonyl-cyclopent-1-enyl)-2-phenethyl-1H-indole-6-carboxylic acid or a pharmaceutically acceptable salt thereof;

3-(2-methoxycarbonyl-cyclopent-1-enyl)-1-methyl-2-phenethyl-1H-indole-6-carboxylic acid or a pharmaceutically acceptable salt thereof;

1-ethoxycarbonylmethyl-3-(2-methoxycarbonyl-cyclopent-1-enyl)-2-phenethyl-1H-indole-6-carboxylic acid or a pharmaceutically acceptable salt thereof;

1-carboxymethyl-3-(2-methoxycarbonyl-cyclopent-1-enyl)-2-phenethyl-1H-indole-6-carboxylic acid or a pharmaceutically acceptable salt thereof;

1-(4-methoxycarbonyl-benzyl)-3-(2-methoxycarbonyl-cyclopent-1-enyl)-2-phenethyl-1H-indole-6-carboxylic acid or a pharmaceutically acceptable salt thereof;

1-biphenyl-4-ylmethyl-3-(2-methoxycarbonyl-cyclopent-1-enyl)-2-phenethyl-1H-indole-6-carboxylic acid or a pharmaceutically acceptable salt thereof;

3-(2-methoxycarbonyl-cyclopent-1-enyl)-2-[3-(3-methoxycarbonyl-phenoxy)-propyl]-1H-indole-6-carboxylic acid or a pharmaceutically acceptable salt thereof;

3-(2-methoxycarbonyl-cyclopent-1-enyl)-2-[3-(3-methoxycarbonyl-phenoxy)-propyl]-1-methyl-1H-indole-6-carboxylic acid or a pharmaceutically acceptable salt thereof;

1-ethoxycarbonylmethyl-3-(2-methoxycarbonyl-cyclopent-1-enyl)-2-[3-(3-methoxycarbonyl-phenoxy)-propyl]-1H-indole-6-carboxylic acid or a pharmaceutically acceptable salt thereof;

1-carboxymethyl-3-(2-methoxycarbonyl-cyclopent-1-enyl)-2-[3-(3-methoxycarbonyl-phenoxy)-propyl]-1H-indole-6-carboxylic acid or a pharmaceutically acceptable salt thereof;

1-(4-methoxycarbonyl-benzyl)-3-(2-methoxycarbonyl-cyclopent-1-enyl)-2-[3-(3-methoxycarbonyl-phenoxy)-propyl]-1H-indole-6-carboxylic acid or a pharmaceutically acceptable salt thereof;

1-biphenyl-4-ylmethyl-3-(2-methoxycarbonyl-cyclopent-1-enyl)-2-[3-(3-methoxycarbonyl-phenoxy)-propyl]-1H-indole-6-carboxylic acid or a pharmaceutically acceptable salt thereof;

2-{[(4-methoxy-benzoyl)-methyl-amino]-methyl}-3-(2-methoxycarbonyl-cyclopent-1-enyl)-1H-indole-6-carboxylic acid or a pharmaceutically acceptable salt thereof;

2-{[(4-methoxy-benzoyl)-methyl-amino]-methyl}-3-(2-methoxycarbonyl-cyclopent-1-enyl)-1-methyl-1H-indole-6-carboxylic acid or a pharmaceutically acceptable salt thereof;

1-ethoxycarbonylmethyl-2-{[(4-methoxy-benzoyl)-methyl-amino]-methyl}-3-(2-methoxycarbonyl-cyclopent-1-enyl)-1H-indole-6-carboxylic acid or a pharmaceutically acceptable salt thereof;

1-carboxymethyl-2-{[(4-methoxy-benzoyl)-methyl-amino]-methyl}-3-(2-methoxycarbonyl-cyclopent-1-enyl)-1H-indole-6-carboxylic acid or a pharmaceutically acceptable salt thereof;

2-{[(4-methoxy-benzoyl)-methyl-amino]-methyl}-1-(4-methoxycarbonyl-benzyl)-3-(2-methoxycarbonyl-cyclopent-1-enyl)-1H-indole-6-carboxylic acid or a pharmaceutically acceptable salt thereof;

1-biphenyl-4-ylmethyl-2-{[(4-methoxy-benzoyl)-methyl-amino]-methyl}-3-(2-methoxycarbonyl-cyclopent-1-enyl)-1H-indole-6-carboxylic acid or a pharmaceutically acceptable salt thereof;

2-butyl-3-(5-methoxy-3,4-dihydro-naphthalen-1-yl)-1H-indole-6-carboxylic acid or a pharmaceutically acceptable salt thereof;

2-butyl-3-(5-methoxy-3,4-dihydro-naphthalen-1-yl)-1-methyl-1H-indole-6-carboxylic acid or a pharmaceutically acceptable salt thereof;

2-butyl-1-ethoxycarbonylmethyl-3-(5-methoxy-3,4-dihydro-naphthalen-1-yl)-1H-indole-6-carboxylic acid or a pharmaceutically acceptable salt thereof;

2-butyl-1-carboxymethyl-3-(5-methoxy-3,4-dihydro-naphthalen-1-yl)-1H-indole-6-carboxylic acid or a pharmaceutically acceptable salt thereof;

2-butyl-1-(4-methoxycarbonyl-benzyl)-3-(5-methoxy-3,4-dihydro-naphthalen-1-yl)-1H-indole-6-carboxylic acid or a pharmaceutically acceptable salt thereof;

3-(5-methoxy-3,4-dihydro-naphthalen-1-yl)-2-phenyl-1H-indole-6-carboxylic acid or a pharmaceutically acceptable salt thereof;

3-(5-methoxy-3,4-dihydro-naphthalen-1-yl)-1-methyl-2-phenyl-1H-indole-6-carboxylic acid or a pharmaceutically acceptable salt thereof;

1-ethoxycarbonylmethyl-3-(5-methoxy-3,4-dihydro-naphthalen-1-yl)-2-phenyl-1H-indole-6-carboxylic acid or a pharmaceutically acceptable salt thereof;

1-carboxymethyl-3-(5-methoxy-3,4-dihydro-naphthalen-1-yl)-2-phenyl-1H-indole-6-carboxylic acid or a pharmaceutically acceptable salt thereof;

1-(4-methoxycarbonyl-benzyl)-3-(5-methoxy-3,4-dihydro-naphthalen-1-yl)-2-phenyl-1H-indole-6-carboxylic acid or a pharmaceutically acceptable salt thereof;

3-(5-methoxy-3,4-dihydro-naphthalen-1-yl)-2-phenethyl-1H-indole-6-carboxylic acid or a pharmaceutically acceptable salt thereof;

3-(5-methoxy-3,4-dihydro-naphthalen-1-yl)-1-methyl-2-phenethyl-1H-indole-6-carboxylic acid or a pharmaceutically acceptable salt thereof;

1-ethoxycarbonylmethyl-3-(5-methoxy-3,4-dihydro-naphthalen-1-yl)-2-phenethyl-1H-indole-6-carboxylic acid or a pharmaceutically acceptable salt thereof;

1-carboxymethyl-3-(5-methoxy-3,4-dihydro-naphthalen-1-yl)-2-phenethyl-1H-indole-6-carboxylic acid or a pharmaceutically acceptable salt thereof;

1-(4-methoxycarbonyl-benzyl)-3-(5-methoxy-3,4-dihydro-naphthalen-1-yl)-2-phenethyl-1H-indole-6-carboxylic acid or a pharmaceutically acceptable salt thereof;

2-[3-(3-methoxycarbonyl-phenoxy)-propyl]-3-(5-methoxy-3,4-dihydro-naphthalen-1-yl)-1H-indole-6-carboxylic acid or a pharmaceutically acceptable salt thereof;

2-[3-(3-methoxycarbonyl-phenoxy)-propyl]-3-(5-methoxy-3,4-dihydro-naphthalen-1-yl)-1-methyl-1H-indole-6-carboxylic acid or a pharmaceutically acceptable salt thereof;

1-ethoxycarbonylmethyl-2-[3-(3-methoxycarbonyl-phenoxy)-propyl]-3-(5-methoxy-3,4-dihydro-naphthalen-1-yl)-1H-indole-6-carboxylic acid or a pharmaceutically acceptable salt thereof;

1-carboxymethyl-2-[3-(3-methoxycarbonyl-phenoxy)-propyl]-3-(5-methoxy-3,4-dihydro-naphthalen-1-yl)-1H-indole-6-carboxylic acid or a pharmaceutically acceptable salt thereof;

1-(4-methoxycarbonyl-benzyl)-2-[3-(3-methoxycarbonyl-phenoxy)-propyl]-3-(5-methoxy-3,4-dihydro-naphthalen-1-yl)-1H-indole-6-carboxylic acid or a pharmaceutically acceptable salt thereof;

2-{[(4-methoxy-benzoyl)-methyl-amino]-methyl}-3-(5-methoxy-3,4-dihydro-naphthalen-1-yl)-1H-indole-6-carboxylic acid or a pharmaceutically acceptable salt thereof;

2-{[(4-methoxy-benzoyl)-methyl-amino]-methyl}-3-(5-methoxy-3,4-dihydro-naphthalen-1-yl)-1-methyl-1H-indole-6-carboxylic acid or a pharmaceutically acceptable salt thereof;

1-ethoxycarbonylmethyl-2-{[(4-methoxy-benzoyl)-methyl-amino]-methyl}-3-(5-methoxy-3,4-dihydro-naphthalen-1-yl)-1H-indole-6-carboxylic acid or a pharmaceutically acceptable salt thereof;

1-carboxymethyl-2-{[(4-methoxy-benzoyl)-methyl-amino]-methyl}-3-(5-methoxy-3,4-dihydro-naphthalen-1-yl)-1H-indole-6-carboxylic acid or a pharmaceutically acceptable salt thereof;

2-{[(4-methoxy-benzoyl)-methyl-amino]-methyl}-1-(4-methoxycarbonyl-benzyl)-3-(5-methoxy-3,4-dihydro-naphthalen-1-yl)-1H-indole-6-carboxylic acid or a pharmaceutically acceptable salt thereof 2-butyl-3-(4-phenyl-cyclohex-1-enyl)-1H-indole-6-carboxylic acid or a pharmaceutically acceptable salt thereof;

2-butyl-1-methyl-3-(4-phenyl-cyclohex-1-enyl)-1H-indole-6-carboxylic acid or a pharmaceutically acceptable salt thereof;

2-butyl-1-carboxymethyl-3-(4-phenyl-cyclohex-1-enyl)-1H-indole-6-carboxylic acid or a pharmaceutically acceptable salt thereof;

2-butyl-1-(4-methoxycarbonyl-benzyl)-3-(4-phenyl-cyclohex-1-enyl)-1H-indole-6-carboxylic acid or a pharmaceutically acceptable salt thereof;

2-cyclopentyl-3-(4-phenyl-cyclohex-1-enyl)-1H-indole-6-carboxylic acid or a pharmaceutically acceptable salt thereof;

2-cyclopentyl-1-methyl-3-(4-phenyl-cyclohex-1-enyl)-1H-indole-6-carboxylic acid or a pharmaceutically acceptable salt thereof;

2-cyclopentyl-1-ethoxycarbonylmethyl-3-(4-phenyl-cyclohex-1-enyl)-1H-indole-6-carboxylic acid or a pharmaceutically acceptable salt thereof;

1-carboxymethyl-2-cyclopentyl-3-(4-phenyl-cyclohex-1-enyl)-1H-indole-6-carboxylic acid or a pharmaceutically acceptable salt thereof 2-cyclopentyl-1-(4-methoxycarbonyl-benzyl)-3-(4-phenyl-cyclohex-1-enyl)-1H-indole-6-carboxylic acid or a pharmaceutically acceptable salt thereof;

2-phenyl-3-(4-phenyl-cyclohex-1-enyl)-1H-indole-6-carboxylic acid or a pharmaceutically acceptable salt thereof;

1-methyl-2-phenyl-3-(4-phenyl-cyclohex-1-enyl)-1H-indole-6-carboxylic acid or a pharmaceutically acceptable salt thereof;

1-ethoxycarbonylmethyl-2-phenyl-3-(4-phenyl-cyclohex-1-enyl)-1H-indole-6-carboxylic acid or a pharmaceutically acceptable salt thereof;

1-carboxymethyl-2-phenyl-3-(4-phenyl-cyclohex-1-enyl)-1H-indole-6-carboxylic acid or a pharmaceutically acceptable salt thereof;

1-(4-methoxycarbonyl-benzyl)-2-phenyl-3-(4-phenyl-cyclohex-1-enyl)-1H-indole-6-carboxylic acid or a pharmaceutically acceptable salt thereof;

2-phenethyl-3-(4-phenyl-cyclohex-1-enyl)-1H-indole-6-carboxylic acid or a pharmaceutically acceptable salt thereof;

1-methyl-2-phenethyl-3-(4-phenyl-cyclohex-1-enyl)-1H-indole-6-carboxylic acid or a pharmaceutically acceptable salt thereof;

1-ethoxycarbonylmethyl-2-phenethyl-3-(4-phenyl-cyclohex-1-enyl)-1H-indole-6-carboxylic acid or a pharmaceutically acceptable salt thereof;

1-carboxymethyl-2-phenethyl-3-(4-phenyl-cyclohex-1-enyl)-1H-indole-6-carboxylic acid or a pharmaceutically acceptable salt thereof;

1-(4-methoxycarbonyl-benzyl)-2-phenethyl-3-(4-phenyl-cyclohex-1-enyl)-1H-indole-6-carboxylic acid or a pharmaceutically acceptable salt thereof;

2-[3-(3-methoxycarbonyl-phenoxy)-propyl]-3-(4-phenyl-cyclohex-1-enyl)-1H-indole-6-carboxylic acid or a pharmaceutically acceptable salt thereof;

2-[3-(3-methoxycarbonyl-phenoxy)-propyl]-1-methyl-3-(4-phenyl-cyclohex-1-enyl)-1H-indole-6-carboxylic acid or a pharmaceutically acceptable salt thereof;

1-carboxymethyl-2-[3-(3-methoxycarbonyl-phenoxy)-propyl]-3-(4-phenyl-cyclohex-1-enyl)-1H-indole-6-carboxylic acid or a pharmaceutically acceptable salt thereof;

1-(4-methoxycarbonyl-benzyl)-2-[3-(3-methoxycarbonyl-phenoxy)-propyl]-3-(4-phenyl-cyclohex-1-enyl)-1H-indole-6-carboxylic acid or a pharmaceutically acceptable salt thereof;

2-{[(4-methoxy-benzoyl)-methyl-amino]-methyl}-3-(4-phenyl-cyclohex-1-enyl)-1H-indole-6-carboxylic acid or a pharmaceutically acceptable salt thereof 2-{[(4-methoxy-benzoyl)-methyl-amino]-methyl}-1-methyl-3-(4-phenyl-cyclohex-1-enyl)-1H-indole-6-carboxylic acid or a pharmaceutically acceptable salt thereof;

1-carboxymethyl-2-{[(4-methoxy-benzoyl)-methyl-amino]-methyl}-3-(4-phenyl-cyclohex-1-enyl)-1H-indole-6-carboxylic acid or a pharmaceutically acceptable salt thereof;

2-{[(4-methoxy-benzoyl)-methyl-amino]-methyl}-1-(4-methoxycarbonyl-benzyl)-3-(4-phenyl-cyclohex-1-enyl)-1H-indole-6-carboxylic acid or a pharmaceutically acceptable salt thereof.

It is understood that the definition of the compounds of formula (I), when $R^1$, $R^2$, $R^3$, and $R^4$ contain asymmetric carbons, encompasses all possible stereoisomers and mixtures thereof. In particular, it encompasses racemic modifications and any optical isomers. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Carboxylic acid salts of the compounds of this invention may be formed with bases such as alkali metals (Na, K, Li) or the alkaline earth metals (Ca or Mg).

Process of the Invention

The compounds of the present invention may be prepared according to the general process outlined below in Scheme I.

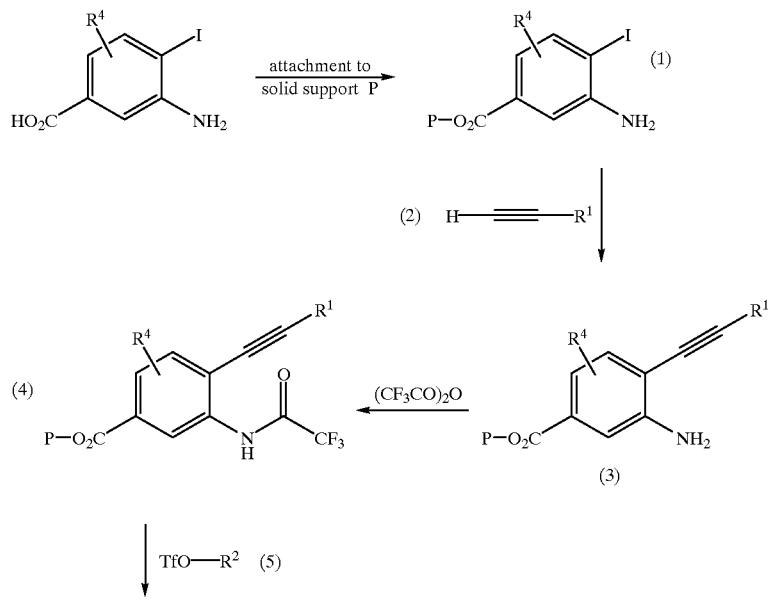

Scheme I

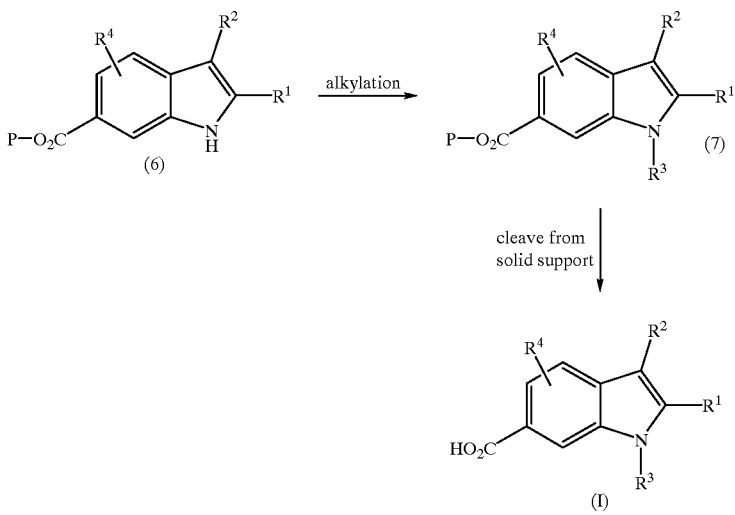

Thus, a substituted 3-amino-4-iodobenzoic acid is attached to the preferred solid support P, a resin of polystyrene crosslinked with divinylbenzene and with a linker such as 4-hydroxymethylphenoxy, most preferably Wang's resin as described below, in the presence of a coupling reagent such as diisopropylcarbodiimide to produce a compound of formula (1). Alternatively, a resin such as Wang resin (Su-Sun Wang, Journal of the American Chemical Society 95(4), 1338–1333, 1973, compound III) is converted to a chloro resin (Scheme II) with lithium chloride, methanesulfonyl chloride, and a base such as collidine or lutidine in a polar aprotic solvent such as dimethylformamide and subsequently reacted with an alkaline metal salt, preferably the cesium salt, of a substituted 3-amino-4-iodobenzoic acid to produce a compound of formula (1).

Scheme II

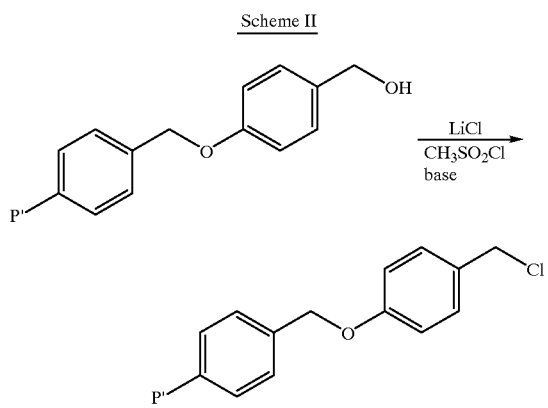

A compound of formula (1) is reacted with a terminal alkyne of formula (2) in the presence of a palladium catalyst, copper(I) iodide, and an amine base in a polar aprotic solvent such as dimethylformamide to yield a compound of formula (3), which is trifluoroacetylated to yield a compound of formula (4). A compound of formula (4) is reacted with a vinyl trifluoromethanesulfonate (5), a palladium catalyst, and potassium carbonate in a polar aprotic solvent such as dimethylformamide to produce a compound of formula (6). A compound of formula (6) is alkylated with an alkylating agent such as an alkyl iodide or an arylalkyl bromide in the presence of a base such as sodium hydride in a polar aprotic solvent such as dimethylformamide to produce a compound of formula (7). The compound of formula (I) wherein $R^1$, $R^2$, $R^3$, and $R^4$ are as defined above is removed from the solid support P with an acidic cleavage mixture such as trifluoroacetic acid in dichloromethane.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration such as parenteral administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. The actual dosage used on an individual shall be determined by a physician following standard medical principles. Conventionally one begins with a low dosage and increases the dosage until a satisfactory pharmacological effect is obtained. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

The present invention further provides a compound of the invention for use as an active therapeutic substance.

Estrogen Receptor Assay: 2X VIT ERE Transfection Assay

Objective: To identify compounds that enhance the expression of luciferase gene activity compared to 17β-estradiol in a transient transfection model. Enhancement of luciferase gene expression in this model is dependent upon estrogen receptor (ER) interaction with a vitellogenin gene estrogen responsive element (ERE) capable of enhancing basal promoter activity. This is a sensitive and rapid methodology to assess estrogenic/antiestrogenic potency of compounds.

Procedure: Cell Maintenace and treatment: Chinese Hamster Ovary cells (CHO) which have been stably transfected with the human estrogen receptor are maintained in DMEM+10% fetal bovine serum (FBS). 48 h prior to treatment the growth medium is replaced with DMEM lacking phenol red+10% dextran coated charcoal stripped FBS (treatment medium). Cells are plated at a density of 5000 cells/well in 96-well plates containing 200 µL of medium/well.

Calcium Phosphate Transfection: Reporter DNA (Promega plasmid pGL2 containing two tandem copies of the vitellogenin ERE in front of the minimal thymidine kinase promoter driving the luciferase gene) is combined with the β-galactosidase expression plasmid pCH110 (Pharmacia) and carrier DNA (pTZ18U) in the following ratio: 10 µg of reporter DNA, 5 µg of pCH110 DNA, 5 µg of pTZ18U, and 20 µg of DNA/1 mL of transfection solution. The DNA (20 µg) is dissolved in 500 µL of 250 mM sterile $CaCl_2$ which is then slowly (dropwise) added to 500 µL of 2× HeBS (0.28 M NaCl, 50 mM HEPES, 1.5 mM $Na_2HPO_4$, pH 7.05) and incubated at room temperature for 20 min. 20 µL of this mixture is added to each well of cells and remains on the cells for 16 h. At the end of this incubation the precipitate is removed, the cells are washed with media, fresh treatment media is replaced and the cells are treated with either vehicle, 1 nM 17β-estradiol, 1 µM compound or 1 µM compound+1 nM 17β-estradiol. Each treatment condition is performed on 8 wells (n=8) which are incubated for 24 h prior to luciferase assay.

Luciferase Assay: After 24 h exposure to compounds, the media is removed and each well is washed 2× with 125 µL of PBS lacking $Mg^{++}$ and $Ca^{++}$. After removing the PBS, 25 µL of Promega lysis buffer is added to each well and allowed to stand at room temperature for 15 min, followed by 15 min at −80° C. and 15 min at 37° C. 20 µL of lysate is tranferred to an opaque 96-well plate for luciferase activity evaluation and the remaining lysate (5 µL) is used for β-galactosidase activity evaluation (normalize transfection). The luciferan substrate (Promega) added is 100 µL aliquots to each well automaticaly by the luminometer and the light produced (relative light units) is read 10 seconds after addition. The data is logged and automatically sent to a JMP statistical program for analysis. A hard copy printout is also produced at the time of the assay.

β-galactosidase Assay: To the remaining 5 µL of lysate 45 µL of PBS is added. 50 µl of Promega β-galactosidase 2× assay buffer is added, mixed well and incubated at 37° C. for 1 h. A plate containing a standard curve (0.1 to 1.5 milliunits in triplicate) is set up for each experimental run. The plates are analyzed on a Molecular Devices spectrophotometric plate reader at 410 nm. The optical densities for the unknowns are converted to milliunits of activity by mathematical extrapolation from the standard curve. Analysis of Results: The luciferase data is generated as relative light units (RLUs) accumulated during a 10 second measurement and is automatically transferred to a JMP (SAS Inc) file where background RLUs are subtracted. The β-galactosidase values are automatically imported into the file and these values are divided into the RLUs to normalize the data. The mean and standard deviation is determined from a n=8 for each treatment. Compound activity is compared to 17β-estradiol for each plate. Percentage of activity as compared to 17β-estradiol is calculated as follows:

%=((Estradiol value-control value)/(compound value))×100

For example, at a concentration of 1 µM, the compound 1-ethoxycarbonylmethyl-3-(2-methoxycarbonyl-cyclopent-1-enyl)-2-phenyl-1H-indole-6-carboxylic acid had 25% of the activity of 17β-estradiol (at 1 nM) and is therefore estrogenic.

Reference Compounds: Various reference compounds (1 µM) were assessed for estrogenic and/or antiestrogenic activity (1 µM compound+1 nM 17β-estradiol) by assaying for luciferase activity and corresponding % values compared to 1 nM 17β-estradiol (set to 100%) were calculated. Note there are three orders of magnitude difference in the dose of reference compounds versus 17β-estradiol concentration:

| | |
|---|---|
| 17β-estradiol | 100% activity |
| estriol | 38% activity |
| estrone | 40% activity |
| tamoxifen (+1 nM estradiol) | <5% activity, (10%) |
| raloxifene (+1 nM estradiol) | <5% activity, (0%) |

At 1 µM dosages the estriol and estrone would be expected to be about 40% as potent as 17β-estradiol in this assay versus the alkaline phosphatase response in Ishikawa cells (Procedure 1501) which is a more complex biological series of events. The lack of independent activity and antiestrogenic activity of tamoxifen and raloxifene was as predicted as consistent with reports in the literature relating to their effects in a rat uterotrophic assay.

Reference: Tzukerman, M. T., Esty, A., Santiso-Mere, D., Danielian, P., Parker, M. G., Stein, R. B., Pike, J. W. and McDonnell, D. P. Human estrogen receptor transactivational capacity is determined by both cellular and promoter context and mediated by two functionally distinct intramolecular regions. *Molecular Endocrinology* 1994, 8, 21–30.

Specific procedures are described in the following experimental examples. These examples are given to illustrate the invention and should not be construed as limiting the invention set forth in the appended claims.

EXAMPLE 1

Preparation of 4-(1-Hexynyl)-3-trifluoroacetamidobenzoic Acid on Wang Resin

Step 1: Chloro-Wang Resin

A mixture of Wang resin (Wang, S. *J. Am. Chem. Soc.* 1973, 95, 1328–1333) (Advanced ChemTech 200–400 mesh, 1% crosslinked; loading: 0.92 mmol/g; 15.0 g, 0.011 mol), LiCl (1.4 g, 0.033 mol) and DMF (150 mL) was magnetically stirred for 40 min. Collidine (4.0 g, 0.033 mol) was added and the mixture was cooled (0–5° C.) with an ice bath. Methanesulfonyl chloride (3.8 g, 0.033 mol) was added over 5 min. After 10 min, the cooling bath was removed and stirring was continued for 68 h. The mixture was filtered and the resin was washed with DMF (250 mL), 30% $H_2O$/DMF ((2×300 mL), DMF (2×250 mL), EtOH (3×250 mL), $CH_2Cl_2$ (3×300 mL), and hexane (2×250 mL). The resin was dried over $P_2O_5$ in vacuo to give 14.3 g; $^{13}C$ NMR (CDCl$_3$) δ 46.22 ($CH_2$Cl); IR (KBr) cm$^{-1}$: 2900, 1600, 1520, 1485, 1450.

Step 2: Attachment of 3-Amino-4-iodobenzoic acid to Wang Resin

To a stirred suspension of 3-amino-4-iodobenzoic acid in EtOH (100 mL) was added $Cs_2CO_3$ (7.5 g, 0.023 mol) and water (30 mL). The solution was concentrated, and azetroped with 3:1 toluene/EtOH and toluene (150 mL) to give 18.7 g of the cesium salt of 3-amino4-iodobenzoic acid as a white solid. A mixture of chloro-Wang resin (27.1 g), prepared as described in step 1 above, cesium salt (18.7 g) and DMF (350 mL) was heated to 50–60° C. for 2.5 days. The mixture was filtered and washed with DMF (2×200 mL), water (2×200 mL), DMF (2×200 mL), EtOH (2×200 mL), and $CH_2Cl_2$. The resin was dried in vacuo to give 30.0 g; IR (KBr) cm$^{-1}$: 1700 (ester CO). Anal. calc'd for N: 1.05%; Found: 1.30%.

To determine the loading, a sample of resin (300 mg) was stirred with 50% TFA/$CH_2Cl_2$ for 3 h, filtered, and the filtrate was concentrated to give 56 mg (95%) of 3-amino-4-iodobenzoic acid. Resin loading: 0.71 mmol/g.

Step 3: Reaction with 1-Hexyne and Trifluoroacetylation

To a mixture of 3-amino-4-iodobenzoic acid on Wang resin (loading 0.6 mmol/g; 3.0 g, 1.8 mmol) and 1-hexyne (0.74 g, 9.0 mmol) in DMF (40 mL) was added bis (triphenylphosphine)palladium(II) chloride (0.20 g, 0.28 mmol) and CuI (0.1 g, 0.52 mmol). The mixture was stirred magnetically for 2 h, filtered, and washed with $CH_2Cl_2$. The resin was suspended in $CH_2Cl_2$ (40 mL), cooled (0° C.), and pyridine (1.5 mL) and trifluoroacetic anhydride (2.6 mL) were added. After 2 h, the mixture was filtered, washed with $CH_2Cl_2$, and dried.

To confirm that the reactions occured, 100 mg of resin was treated with 50% TFA/$CH_2Cl_2$ for 3 h, filtered, and the filtrate was concentrated to give 9.8 mg of 4-(1-hexynyl)-3-trifluoroacetamidobenzoic acid; $^1H$ NMR (DMSO-d$_6$) δ 0.95 (t, 3 H), 1.50 (m, 4 H), 2.95 (m, 2 H), 7.60 (d, 1 H), 7.85 (d, 1 H), 7.90 (s, 1 H), 11.20 (s, 1 H). Anal. calc'd for $C_{15}H_{14}F_3NO_3$: C, 57.51; H, 4.50; N, 4.47; Found: C, 57.20; H, 4.38; N, 4.46.

EXAMPLE 2

Preparation of 4-Cyclopentylacetylenyl-3-trifluoroacetamidobenzoic Acid on Wang Resin The resin product was prepared according to Step 3 of Example 1 from 3-amino-4-iodobenzoic acid on Wang resin and cyclopentylacetylene.

A sample of resin was treated with 50% TFA/ $CH_2Cl_2$ as in Step 3 of Example 1 to yield 4-cyclopentylacetylenyl-3-trifluoroacetamidobenzoic acid; $^1H$ NMR (DMSO-d$_6$) δ 1.65 (m, 6 H), 1.95 (m, 2 H), 2.91 (t, J=6.9 Hz, 1 H), 7.59 (d, J=8.1 Hz, 1 H), 7.86 (d, J=8.1 Hz, 1 H), 7.91 (s, 1 H), 11.13 (s, 1 H).

EXAMPLE 3

Preparation of 4-(2-Phenylacetylenyl)-3-trifluoroacetamidobenzoic Acid on Wang Resin The resin product was prepared according to Step 3 of Example 1 from 3-amino-4-iodobenzoic acid on Wang resin and phenylacetylene.

A sample of resin was treated with 50% TFA/ $CH_2Cl_2$ as in Step 3 of Example 1 to yield 4-(2-phenylacetylenyl)-3-trifluoroacetamidobenzoic acid; $^1H$ NMR (DMSO-d$_6$) δ 7.50 (m, 5 H), 7.79 (d, J=8.1 Hz, 1 H), 7.95 (d, J=8.1 Hz, 1 H), 8.00 (s, 1 H), 11.42 (s, 1 H), 13.40 (br s, 1 H). Anal. calcd for $C_{17}H_{10}F_3NO_3$: C, 61.27; H, 3.02; N, 4.20; Found: C, 59.73; H, 2.76; N, 4.06.

EXAMPLE 4

Preparation of 4-[(4-Phenyl)-1-butynyl]-3-trifluoroacetamidobenzoic Acid on Wang Resin The resin product was prepared according to Step 3 of Example 1 from 3-amino-4-iodobenzoic acid on Wang resin and 4-phenyl-1-butyne.

A sample of resin was treated with 50% TFA/ $CH_2Cl_2$ as in Step 3 of Example 1 to yield 4-[(4-phenyl)-1-butynyl]-3-trifluoroacetamidobenzoic acid; $^1H$ NMR (DMSO-d$_6$) δ 2.75 (t, J=6.6 Hz, 2 H), 2.85 (t, J=6.6 Hz, 2 H), 7.29 (m, 5 H), 7.56 (d, J=8.1 Hz, 1 H), 7.85 (d, J=8.1 Hz, 1 H), 7.93 (s, 1 H), 11.18 (s, 1 H).

EXAMPLE 5

Preparation of 4-[(5-(3-Carbomethoxy)phenoxy)-1-pentynyl]-3-trifluoroacetamidobenzoic Acid on Wang Resin The resin product was prepared according to Step 3 of Example 1 from 3-amino-4-iodobenzoic acid on Wang resin and 5-[(3-carbomethoxy)phenoxy]-1-pentyne.

A sample of resin was treated with 50% TFA/$CH_2Cl_2$ as in Step 3 of Example 1 to yield 4-[5-(3-carbomethoxy)phenoxy-1-pentynyl]-3-trifluoroacetiamidobenzoic acid; $^1H$ NMR (DMSO-d$_6$) δ 2.00 (m, 2 H), 2.66 (t, J=6.6 Hz, 2 H), 3.84 (s, 3 H), 4.15 (t, J=5.7 Hz), 7.23 (d, J=6.9 Hz, 1 H), 7.44 (m, 2 H), 7.55 (d, J=7.5 Hz, 1 H), 7.62 (d, J=8.1 Hz, 1 H), 7.85 (d, J=8.1 Hz, 1 H), 7.93 (s, 1 H), 11.20 (s, 1 H).

EXAMPLE 6

Preparation of 4-[(3-(N-Methyl-N-(4-methoxybenzoyl)-amino)-1-propynyl]-3-trifluoroacetamidobenzoic Acid on Wang Resin The resin product was prepared according to Step 3 of Example 1 from 3-amino-4-iodobenzoic acid on Wang resin and N-methyl-N-(4-methoxybenzoyl)propargylamine.

A sample of resin was treated with 50% TFA/$CH_2Cl_2$ as in Step 3 of Example 1 to yield 4-[(3-(N-Methyl-N-(4-methoxybenzoyl)-amino)-1-propynyl]-3- trifluoroacetamidobenzoic acid; $^1$H NMR (DMSO-d$_6$) δ 3.03 (s, 3 H), 3.80 (s, 3 H), 7.00 (d, J=8.6 Hz, 2 H), 7.44 (d, J=8.6 Hz, 2 H), 7.71 (d, J=8.1 Hz, 1 H), 7.86 (d, J=8.1 Hz, 1 H), 7.95 (s, 1 H), 11.33 (s, 1 H).

EXAMPLE 7

Parallel Synthesis of Six Indole Compounds

Six compounds were synthesized in parellel in a HPS-1 multiple peptide synthesizer (CoshiSoft/PeptiSearch, Tuscon, Ariz.). One of each of the resins prepared according to Examples 1–6 was placed in a reaction vessel in the synthesizer (100 mg per vessel, 0.06 mmol): 4-(1-hexynyl)-3-trifluoroacetamidobenzoic acid on Wang resin in vessel 1; 4-cyclopentylacetylenyl-3-trifluoroacetamidobenzoic acid on Wang resin in vessel 2; 4-(2-phenylacetylenyl)-3-trifluoroacetamidobenzoic acid on Wang resin in vessel 3; 4-[(4-phenyl)-1-butynyl]-3-trifluoroacetamidobenzoic acid on Wang resin in vessel 4; 4-[(5-(3-carbomethoxy) phenoxy)-1-pentynyl]-3-trifluoroacetamidobenzoic acid on Wang resin in vessel 5; and 4-[(3-(N-methyl-N-(4-methoxybenzoyl)-amino)-1-propynyl]-3-trifluoroacetamidobenzoic acid on Wang resin in vessel 6. To each vessel was added potassium carbonate (70 mg), a solution of (2-carboxymethyl)-1-cyclopentenyl trifluoromethanesulfonate (82 mg, 0.30 mmol; prepared according to Piers et al. *Tetrahedron Lett.* 1984, 25, 3155) in dimethylformamide (1.0 mL), and a solution of tetrakis (triphenylphosphine)palladium(O) in dimethylformamide (1.0 mL). The synthesizer was rotated at room temperature on a Roto-Torque heavy duty rotator (Cole-Parmer) for 18 h. The mixtures were filtered and the resin in each vessel was washed with water (1×1.5 mL), dimethylformamide (3×1.5 mL), and dichloromethane (4×1.5 mL). The resins were dried under vacuum.

The products were cleaved from the solid support according to the following procedure. To each vessel was added 3:1 trifluoroacetic acid/dichloromethane (1.5 mL). The HPS-1 synthesizer was left standing for 1 h, and the solutions were filtered into 1 dram vials. The resin in each vessel was washed with dichloromethane (1 mL) and diethyl ether (1 mL). The solutions were concentrated under a nitrogen stream and dried over P$_2$O$_5$ under vacuum.

Spectral data for individual compounds:

EXAMPLE 7-1

2-Butyl-3-(2-methoxycarbonyl-cyclopent-1-enyl)-1H-indole-6-carboxylic Acid $^1$H NMR (DMSO-d$_6$) δ 0.85 (t, J=7.2 Hz, 3 H), 1.24 (q, J=7.5 Hz, 2 H), 1.61 (m, 2 H), 1.95 (m, 2 H), 2.62 (t, J=7.5 Hz, 2 H), 2.75 (t, J=7.2 Hz, 2 H), 2.82 (t, J=7.2 Hz, 2 H), 3.45 (s, 3 H), 7.28 (d, J=8.3 Hz, 1 H), 7.54, J=8.3, 0.9 Hz, 1 H), 7.90 (d, J=0.9 Hz, 1 H), 11.44 (s, 1 H); MS: (CI) [M+H]$^+$ m/z=342.

EXAMPLE 7-2

2-Cyclopentyl-3-(2-methoxycarbonyl-cyclopent-1-enyl)-1H-indole-6-carboxylic Acid $^1$H NMR (DMSO-d$_6$) δ 1.66 (m, 4 H), 1.81 (m, 2 H), 1.96 (m, 4 H), 2.76 (m, 4 H), 3.06 (m, 1 H), 3.43 (s, 3 H), 7.23 (d, J=8.3 Hz, 1 H), 7.53 (dd, J=8.3, 1.1 Hz, 1 H), 7.92 (d, J=1.1 Hz, 1 H), 11.30 (s, 1 H); MS: (EI) M$^+$ m/z=353.

EXAMPLE 7-3

3-(2-Methoxycarbonyl-cyclopent-1-enyl)-2-phenyl-1H-indole-6-carboxylic Acid $^1$H NMR (DMSO-d$_6$) δ 1.92 (m, 2 H), 2.63 (t, J=5.5 Hz, 2 H), 2.76 (t, J=7.2 Hz, 2 H), 3.29 (s, 3 H), 7.28 (d, J=8.6 Hz, 1 H), 7.39 (m, 1 H), 7.49 (m, 2 H), 7.60 (m, 3 H), 8.02 (d, J=0.9 Hz, 1 H), 11.90 (s, 1 H); MS: (CI) [M+H]$^+$ m/z=362.

EXAMPLE 7-4

3-(2-Methoxycarbonyl-cyclopent-1-enyl)-2-phenethyl-1H-indole-6-carboxylic Acid $^1$H NMR (DMSO-d$_6$) δ 1.87 (m, 2 H), 2.60 (m, 2 H), 2.72 (t, J=7.9 Hz, 2 H), 2.93 (m, 4 H), 3.46 (s, 3 H), 7.09 (d, J=6.8 Hz, 1 H), 7.14 (m, 1 H), 7.22 (m, 1 H), 7.28 (d, J=8.3 Hz, 1 H), 7.54 (dd, J=8.3, 1.5 Hz, 1 H), 7.92 (d, J=1.5 Hz, 1 H), 11.59 (s, 1 H); MS: (EI) M$^+$ m/z=389.

EXAMPLE 7-5

3-(2-Methoxycarbonyl-cyclopent-1-enyl)-2-[3-(3-methoxycarbonyl-phenoxy)-propyl]-1H-indole-6-carboxylic Acid $^1$H NMR (DMSO-d$_6$) δ 1.80 (m, 2 H), 2.08 (m, 2 H), 2.56 (m, 2 H), 2.72 (m, 2 H), 2.85 (t, J=7.5 Hz, 2 H), 3.40 (s, 3 H), 3.82 (s, 3 H), 3.92 (t, J=5.9 Hz, 2 H), 7.15 (m, 1 H), 7.22 (d, J=8.6 Hz, 1 H), 7.35 (m, 1 H), 7.40 (m, 1 H), 7.52 (m, 2 H), 7.91 (d, J=0.9Hz, 1 H), 11.54 (s, 1 H); MS: (EI) M$^+$ m/z=477.

EXAMPLE 7-6

2-{[(4-Methoxy-benzoyl)-methyl-amino]-methyl}-3-(2-methoxycarbonyl-cyclopent-1-enyl)-1H-indole-6-carboxylic Acid $^1$H NMR (DMSO-d$_6$) δ 1.93 (m, 2 H), 2.73 (m, 2 H), 2.78 (s, 3 H), 3.51 (m, 2 H), 3.77 (s, 6 H), 4.65 (m, 2 H), 6.97 (d, J=8.8 Hz, 2 H), 7.39 (d, J=8.3 Hz, 1 H), 7.43 (d, J=8.8 Hz, 2 H), 7.58 (dd, J=8.3, 0.7 Hz, 1 H), 8.04 (d, J=0.7 Hz, 1 H), 11.50 (br s, 2 H); MS: (EI) M$^+$ m/z=462.

EXAMPLE 8

2-Phenyl-3-(4-phenyl-cyclohex-1-enyl)-1H-indole-6-carboxylic Acid

Step 1: 4-Phenylcyclohex-1-enyl Trifluoromethanesulfonate

The title compound was prepared from 4-phenylcyclohexanone according to the procedure of Piers et al. *Tetrahedron Lett.* 1984, 25, 3155; $^1$H NMR (DMSO-d$_6$) δ 1.95 (m, 2 H), 2.35 (m, 3 H), 2.50 (m, 1 H), 2.81 (m, 1 H), 5.79 (t, J=2.4 Hz, 1 H), 7.22 (m, 1 H), 7.29 (m, 5 H).

Step 2: 2-Phenyl-3-(4-phenyl-cyclohex-1-enyl)-1H-indole-6-carboxylic Acid

The title compound was prepared according to the procedure outlined in Example 7, employing 4-(2-phenylacetylenyl)-3-trifluoroacetamidobenzoic acid on Wang resin (prepared according to Example 3) and 4-phenylcyclohex-1-enyl trifluoromethanesulfonate; ¹H NMR (DMSO-d₆) δ 1.90 (m, 2 H), 2.40 (m, 3 H), 3.00 (m, 1 H), 5.90 (m, 1 H), 7.20 (m, 1 H), 7.30 (m, 5 H), 7.50 (m, 2 H), 7.75 (m, 5 H), 7.95 (m, 1 H), 11.60 (s, 1 H).

EXAMPLE 9

2-Butyl-3-(5-methoxy-3,4-dihydro-naphthalen-1-yl)-1H-indole-6-carboxylic Acid

Step 1: 5-Methoxy-3,4-dihydro-naphthalen-1-yl Trifluoromethanesulfonate

The title compound was prepared from 5-methoxy-3,4-dihydronaphthalene-1-one according to the procedure of Piers et al. *Tetrahedron Lett.* 1984, 25, 3155; ¹H NMR (DMSO-d₆) δ 2.47 (m, 2 H), 2.75 (t, J=8.2 Hz, 2 H), 6.21 (t, J=4.8 Hz, 2 H), 6.87 (d, J=7.6 Hz, 1 H), 7.07 (d, J=8.2 Hz, 1 H), 7.31 (m, 1 H).

Step 2: 2-Butyl-3-(5-methoxy-3,4-dihydro-naphthalen-1-yl)-1H-indole-6-carboxylic Acid The title compound was prepared according to the procedure outlined in Example 7, employing 4-(1-hexynyl)-3-trifluoroacetamidobenzoic acid on Wang resin (prepared according to Example 1) and 5-methoxy-3,4-dihydro-naphthalen-1-yl trifluoromethanesulfonate; ¹H NMR (DMSO-d₆) δ 0.80 (t, 3 H), 1.22 (m, 2 H), 1.60 (m, 2 H), 2.39 (m, 2 H), 2.70 (m, 4 H), 3.80 (s, 3 H), 6.02 (t, 1 H), 6.32 (d, 1 H), 6.85 (d, 1 H), 6.98 (m, 1 H), 7.08 (d, 1 H), 7.50 (d, 1 H), 7.95 (s, 1 H), 11.40 (s, 1 H).

EXAMPLE 10

2-{[(4-Methoxy-benzoyl)-methyl-amino]-methyl}-3-(benzocyclohept-1-enyl)-1H-indole-6-carboxylic Acid Step 1: Benzocyclohept-1-enyl Trifluoromethanesulfonate The title compound was prepared from benzosuberone according to the procedure of Piers et al. *Tetrahedron Lett.* 1984, 25, 3155.

Step 2: 2-{[(4-Methoxy-benzoyl)-methyl-amino]-methyl}-3-(benzocyclohept-1-enyl)-1H-indole-6-carboxylic Acid The title compound was prepared according to the procedure outlined in Example 7, employing 4-[(3-(N-methyl-N-(4-methoxybenzoyl)-amino)-1-propynyl]-3-trifluoroacetamidobenzoic acid on Wang resin (prepared according to Example 6) and benzocyclohept-1-enyl trifluoromethanesulfonate; ¹H NMR (DMSO-d₆) δ 1.98 (m, 2 H), 2.17 (m, 2 H), 2.75 (m, 2 H), 2.85 (s, 3 H), 3.78 (s, 3 H), 4.60 (br s, 2 H), 6.20 (m, 1 H), 6.95 (m, 3 H), 7.05 (m, 1 H), 7.20 (m, 1 H), 7.32 (d, 1 H), 7.40 (m, 3 H), 7.75 (m, 1 H), 8.05 (s, 1 H).

EXAMPLE 11

1-Benzyl-2-butyl-3-(2-methoxycarbonyl-cyclopent-1-enyl)-1H-indole-6-carboxylic Acid To a suspension of 2-butyl-3-(2-methoxycarbonyl-cyclopent-1-enyl)-1H-indole-6-carboxylic acid on Wang resin (100 mg; compound 7-1, prepared according to the procedure outlined in Example 7) in dimethylformamide (1.5 mL) was added sodium hydride (60% in mineral oil; 20 mg) and the mixture was stirred at room temperature for 30 min. Benzyl bromide (0.1 mL) was added and the mixture was stirred for 3 h. The mixture was filtered, washed with water (1×1.5 mL), tetrahydrofuran (2×1.5 mL), dichloromethane (2×1.5 mL), and dried. The product was cleaved from the resin by treatment with 1:1 trifluoroacetic acid/dichloromethane for 1 h; ¹H NMR (DMSO-d₆) δ 0.76 (t, 3 H), 1.20 (m, 2 H), 1.98 (m, 2 H), 2.00 (m, 2 H), 2.68 (t, 2 H), 2.82 (m, 4 H), 3.43 (s, 3 H), 5.56 (s, 2 H), 6.96 (d, 2 H), 7.30 (m, 4 H), 7.60 (d, 1 H), 7.90 (s, 1 H).

EXAMPLE 12

1-Ethoxycarbonylmethyl-3-(2-methoxycarbonyl-cyclopent-1-enyl)-2-phenyl-1H-indole-6-carboxylic Acid To a suspension of 3-(2-methoxycarbonyl-cyclopent-1-enyl)-2-phenyl-1H-indole-6-carboxylic acid on Wang resin (100 mg; compound 7-3, prepared according to the is procedure outlined in Example 7) in dimethylformamide (1.5 mL) was added sodium hydride (60% in mineral oil; 20 mg) and the mixture was stirred at room temperature for 30 min. Ethyl bromoacetate (0.1 mL) was added and the mixture was stirred for 3 h. The mixture was filtered, washed with water (1×1.5 mL), tetrahydrofuran (2×1.5 mL), dichloromethane (2×1.5 mL), and dried. The product was cleaved from the resin by treatment with 1:1 trifluoroacetic acid/dichloromethane for 1 h; ¹H NMR (DMSO-d₆) δ 1.13 (t, J=7.1 Hz, 3 H), 1.80 (m, 2 H), 2.50 (m, 2 H), 2.63 (m, 2 H), 3.33 (s, 3 H), 4.09 (q, J=7.1 Hz, 7.30 (m, 2 H), 7.39 (d, J=8.5 Hz, 1 H), 7.48 (m, 3 H), 7.71 (d, J=7.2 Hz, 1 H), 8.11 (s, 1 H).

EXAMPLE 13

1-Benzyl-2-butyl-3-(5-methoxy-3,4-dihydro-naphthalen-1-yl)-1H-indole-6-carboxylic Acid To a suspension of 2-butyl-3-(5-methoxy-3,4-dihydro-naphthalen-1-yl)-1H-indole-6-carboxylic acid on Wang resin (100 mg; prepared according to the procedure outlined in Example 9) in dimethylformamide (1.5 mL) was added sodium hydride (60% in mineral oil; 20 mg) and the mixture was stirred at room temperature for 30 min. Benzyl bromide (0.1 mL) was added and the mixture was stirred for 3 h. The mixture was filtered, washed with water (1×1.5 mL), tetrahydrofuran (2×1.5 mL), dichloromethane (2×1.5 mL), and dried. The product was cleaved from the resin by treatment with 1:1 trifluoroacetic acid/dichloromethane for 1 h; ¹H NMR (DMSO-d₆) δ 0.67 (t, J=7.0 Hz, 3 H), 1.16 (t, J=6.7 Hz, 2 H), 1.34 (t, J=6.7 Hz, 2 H), 2.42 (m, 2 H), 2.55 (m, 2 H), 2.80 (m, 2 H), 3.82 (s, 3 H), 5.59 (s, 2 H), 6.12 (t, 1 H), 6.32 (d, J=7.3 Hz, 1 H), 6.88 (d, J=8.3 Hz, 1 H), 7.00 (m, 3 H), 7.15 (d, J=8.3 Hz, 1 H), 7.30 (m, 3 H), 7.55 (d, J=8.2 Hz, 1 H), 7.94 (s, 1 H).

EXAMPLE 14

1-Ethoxycarbonylmethyl-2-{[(4-methoxy-benzoyl)-methyl-amino]-methyl}-3-(benzocyclohept-1-enyl)-1H-indole-6-carboxylic Acid To a suspension of 2-{[(4-methoxy-benzoyl)-methyl-amino]-methyl}-3-(benzocyclohept-1-enyl)-1H-indole-6- carboxylic acid on Wang resin (100 mg; prepared according to the procedure outlined in Example 10) in dimethylformamide (1.5 mL) was added sodium hydride (60% in mineral oil; 20 mg) and the mixture was stirred at room temperature for 30 min. Ethyl bromoacetate (0.1 mL) was added and the mixture was stirred for 3 h. The mixture was filtered, washed with water (1×1.5 mL), tetrahydrofuran (2×1.5 mL), dichloromethane (2×1.5 mL), and dried. The product was cleaved from the resin by treatment with 1:1 trifluoroacetic acid/dichloromethane for 1 h; $^1$H NMR (DMSO-$d_6$) δ 1.15 (t, 3 H), 2.10 (m, 2 H), 2.20 (m, 2 H), 2.70 (s, 3 H), 2.80 (m, 2 H), 3.80 (s, 3 H), 4.05 (q, 2 H), 4.80 (s, 2 H), 5.20 (br s, 2 H), 6.35 (t, 1 H), 6.80 (d, 1 H), 6.97 (d, 2 H), 7.08 (m, 2 H), 7.20 (m, 1 H), 7.38 (d, 2 H), 7.55 (d, 1 H), 7.80 (d, 1 H), 7.95 (s, 1 H), 11.40 (br s, 1 H).

EXAMPLE 15

Parallel Synthesis of Forty Two Compounds

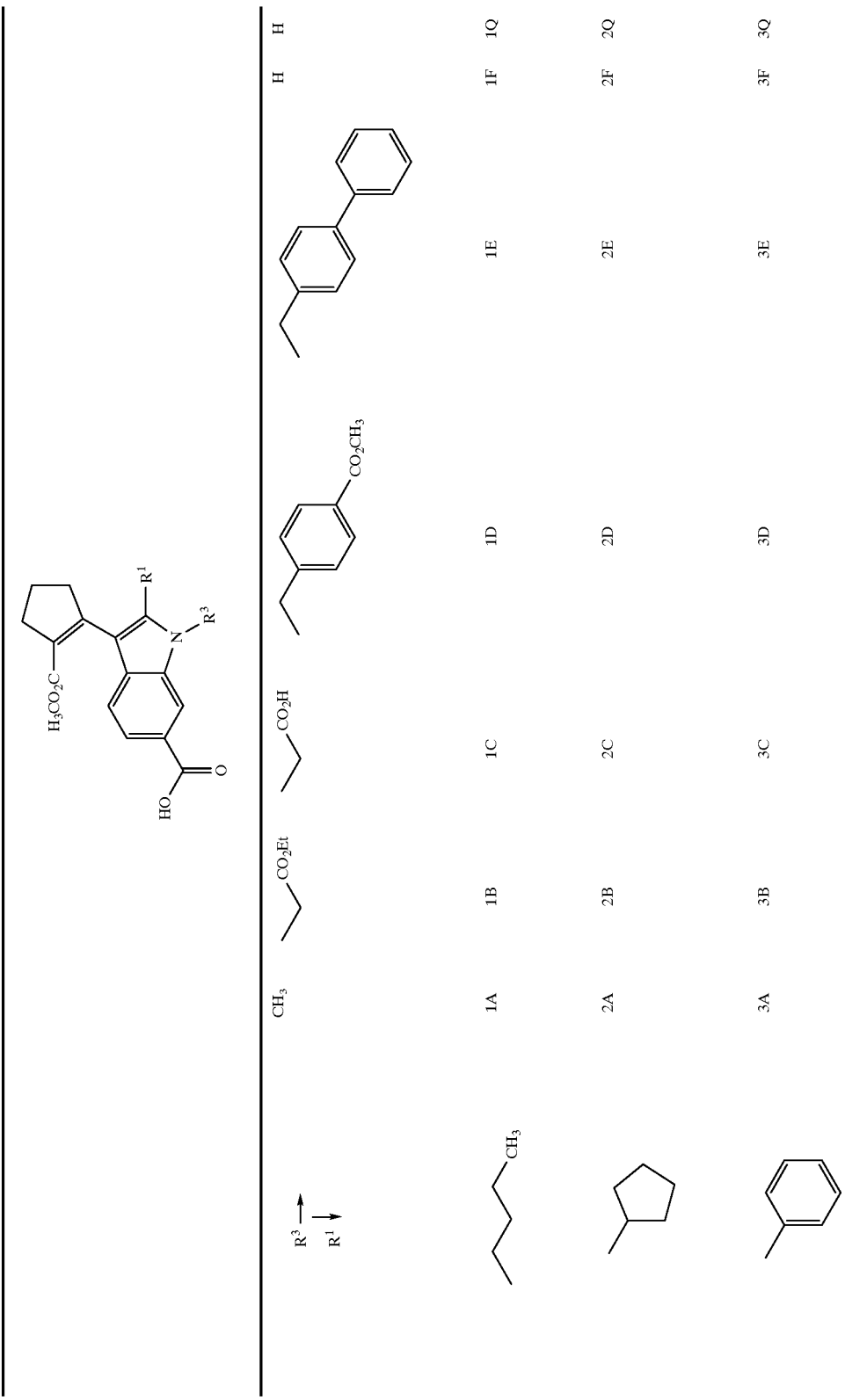

-continued
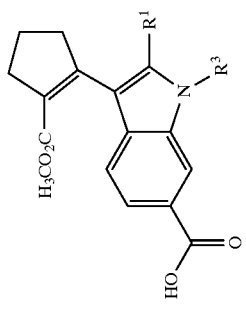
| | | | | | | | |
|---|---|---|---|---|---|---|---|
| 4A | 4B | 4C | 4D | 4E | 4F | 4Q | |
| 5A | 5B | 5C | 5D | 5E | 5F | 5Q | |
| 6A | 6B | 6C | 6D | 6E | 6F | 6Q | |
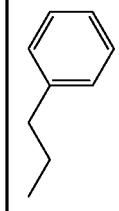
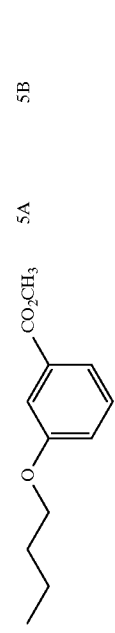
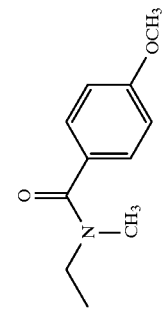

Forty two compounds were synthesized in parallel in a HPS-1 multiple peptide synthesizer with forty two reaction vessels arranged in a 6×7 matrix (CoshiSoft/PeptiSearch, Tuscon, Ariz.). One of each of the resins prepared according to Examples 1–6 was placed in seven reaction vessels (in one row) in the synthesizer (100 mg per vessel, 0.06 mmol): 4-(1-hexynyl)-3-trifluoroacetamidobenzoic acid on Wang resin in row 1; 4-cyclopentylacetylenyl-3-trifluoroacetamidobenzoic acid on Wang resin in row 2; 4-(2-phenylacetylenyl)-3-trifluoroacetamidobenzoic acid on Wang resin in row 3; 4-[(4-phenyl)-1-butynyl]-3-trifluoroacetamidobenzoic acid on Wang resin in row 4; 4-[(5-(3-carbomethoxy)phenoxy)-1-pentynyl]-3-trifluoroacetamidobenzoic acid on Wang resin in row 5; and 4-[(3-(N-methyl-N-(4-methoxybenzoyl)-amino)-1-propynyl]-3-trifluoroacetamidobenzoic acid on Wang resin in row 6. To each vessel was added potassium carbonate (70 mg), a solution of (2-carboxymethyl)-1-cyclopentenyl trifluoromethanesulfonate (82 mg, 0.30 mmol; prepared according to Piers et al. *Tetrahedron Lett.* 1984, 25, 3155) in dimethylformamide (1.0 mL), and a solution of tetrakis(triphenylphosphine)palladium(O) in dimethylformamide (1.0 mL). The synthesizer was rotated at room temperature on a Roto-Torque heavy duty rotator (Cole-Parmer) for 18 h. The mixtures were filtered and the resin in each vessel was washed with water (1×1.5 mL), dimethylformamide (3×1.5 mL), and dichloromethane (4×1.5 mL). The resins were dried under vacuum.

The 6 products from the last column (1Q to 6Q) were cleaved from the solid support for characterization according to the following procedure. To each vessel was added 3:1 trifluoroacetic acid/dichloromethane (1.5 mL). The HPS-1 synthesizer was left standing for 1 h, and the solutions were filtered into 1 dram vials. The resin in each vessel was washed with dichloromethane (1 mL) and diethyl ether (1 mL). The solutions were concentrated under a nitrogen stream and dried over $P_2O_5$ under vacuum. Yields for the products were: 1Q: 7 mg, 2Q: 16 mg, 3Q: 13 mg, 4Q: 14 mg, 5Q: 17 mg, 6Q: 21 mg. The $^1$H NMR spectra of these 6 samples were consistent with the spectra for the compounds listed in Example 7. The 6 products in column F (1F, 2F, 3F, 4F, 5F, 6F) were then cleaved according to the same procedure and retained for biological testing.

The resin in the 30 remaining vessels (columns A through E and rows 1 through 6) were suspended in DMF (1.5 mL per vessel) and approximately 20 mg of sodium hydride (60% suspension in mineral oil) was added to each vessel. After 30 min, methyl iodide was added to the vessels in column A: 1A, 2A, 3A, 4A, 5A, and 6A (0.1 mL per vessel), ethyl bromoacetate was added to the vessels in column B: 1B, 2B, 3B, 4B, 5B, and 6B (0.1 mL per vessel), tert-butyl bromoacetate was added to the vessels in column C: 1C, 2C, 3C, 4C, 5C, and 6C (0.1 mL per vessel), 4-methoxycarbonylbenzyl bromide was added to the vessels in column D: 1D, 2D, 3D, 4D, 5D, and 6D (150 mg per vessel), and 4-phenylbenzyl bromide was added to the vessels in column E: 1E, 2E, 3E, 4E, 5E, and 6E (0.1 mL per vessel). The synthesizer was rotated every 30 min for about 5 min, for a total reaction time of 3 h. The mixtures were filtered and the resin in each vessel was washed with water (1×1.5 mL), tetrahydrofuran (2×1.5 mL), and dichloromethane (2×1.5 mL). The resins were dried under vacuum. The products from the 30 vessels were cleaved from the resins according to the procedure described above. The products from the 30 vessels were analyzed by thin layer chromatography. One major product was observed for the vessels from columns A, C, D, and E. In the vessels from column B, the alkylation reaction with tert-butyl bromoacetate only went to about 50% completion. Yields for the 30 products were:

| 1A: 7 mg  | 1B: 10 mg | 1C: 0 mg  | 1D: 14 mg | 1E: 10 mg |
| 2A: 9 mg  | 2B: 15 mg | 2C: 17 mg | 2D: 10 mg | 2E: 10 mg |
| 3A: 13 mg | 3B: 19 mg | 3C: 19 mg | 3D: 19 mg | 3E: 19 mg |
| 4A: 15 mg | 4B: 16 mg | 4C: 18 mg | 4D: 19 mg | 4E: 12 mg |
| 5A: 15 mg | 5B: 18 mg | 5C: 22 mg | 5D: 12 mg | 5E: 15 mg |
| 6A: 20 mg | 6B: 20 mg | 6C: 20 mg | 6D: 24 mg | 6E: 20 mg |

We claim:

1. A method for the solid phase synthesis of compounds having the formula:

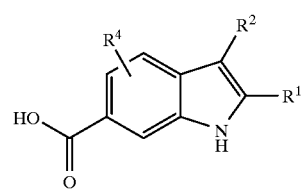

(I)

wherein:

$R^1$ is straight chain alkyl of 1 to 6 carbon atoms, branched chain alkyl of 3 to 7 carbon atoms, cycloalkyl of 3 to 7 carbon atoms, phenyl, phenylalkyl of 7 to 12 carbon atoms, or straight chain alkyl of 1 to 6 carbon atoms substituted with

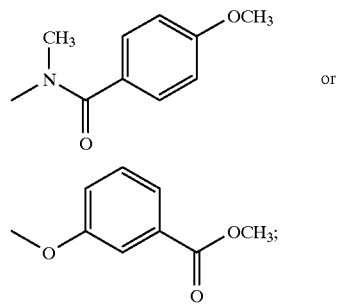

$R^2$ is straight chain alkenyl of 2 to 6 carbon atoms, branched chain alkenyl of 3 to 7 carbon atoms, cycloalkenyl of 3 to 7 carbon atoms, phenyl,

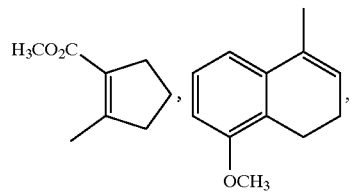

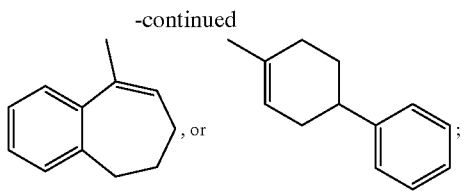, or and $R^4$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

comprising the steps:

a) attaching an $R^4$ substituted 3-amino-4-iodo-benzoic acid of the formula

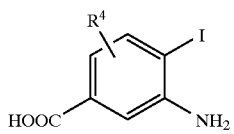

or an alkaline metal salt thereof to a solid support P to produce a compound of formula (1)

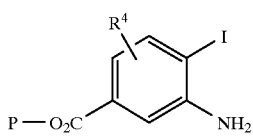 (1)

wherein $R^4$ is defined above;

b) reacting said compound of formula (1) with a terminal alkyne of formula (2)

 (2)

wherein $R^1$ is defined above;

in the presence of a homogenous palladium(O) or palladium (II) catalyst and a secondary or tertiary amine base in a polar aprotic solvent at ambient temperature to produce a compound of formula (3)

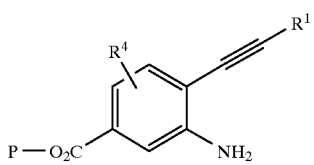 (3)

wherein $R^1$, $R^4$, and P are as defined above; and c) reacting said compound of formula (3) with trifluoroacetic anhydride and an aromatic amine base or a tertiary amine base in dichloromethane to produce a compound of formula (4)

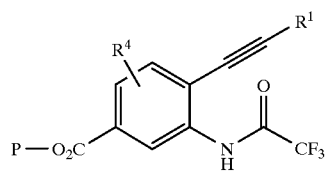 (4)

wherein $R^1$, $R^4$, and P are as defined above; and d) reacting said compound of formula (4) with a vinyl trifluoromethanesulfonate of formula (5)

$$TfO—R^2 \quad (5)$$

wherein $R^2$ defined above;

in the presence of a homogenous palladium(O) or palladium (II) catalyst and an inorganic base in a polar aprotic solvent to produce a compound of formula (6)

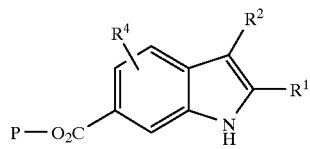 (6)

wherein $R^1$, $R^2$, $R^4$, and P are as defined above, e) reacting said compound of formula (6) with a cleaving reagent to produce a compound of formula (I)

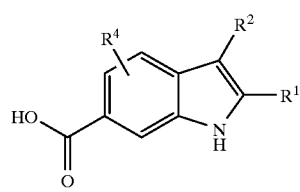 (I)

wherein $R^1$, $R^2$ and $R^4$ are as defined above.

2. The method of claim 1 wherein the solid support used is polystyrene crosslinked with divinylbenzene and functionalized with a linker group.

3. The method according to claim 1 wherein the solid support used is Wang resin.

4. The method according to claim 1 wherein the solid support used is chloro Wang resin and the $R^4$ substituted 3-amino4-iodo-benzoic acid is in the form of an alkaline metal salt of the acid.

5. The method according to claim 4 wherein the alkaline metal salt of the $R^4$ substituted 3-amino-4-iodo-benzoic acid used is the cesium salt.

6. A method for the solid phase synthesis of compounds having the formula:

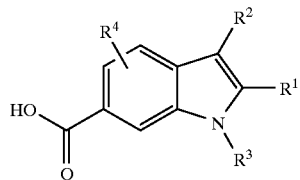
(I)

wherein:

R¹ is straight chain alkyl of 1 to 6 carbon atoms, branched chain alkyl of 3 to 7 carbon atoms, cycloalkyl of 3 to 7 carbon atoms, phenyl, phenylalkyl of 7 to 12 carbon atoms, or straight chain alkyl of 1 to 6 carbon atoms substituted with

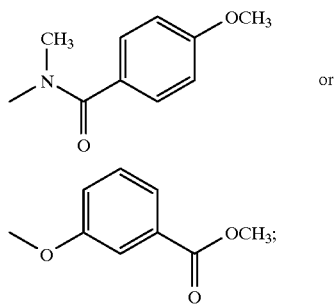
or

R² is straight chain alkenyl of 2 to 6 carbon atoms, branched chain alkenyl of 3 to 7 carbon atoms, cycloalkenyl of 3 to 7 carbon atoms, phenyl,

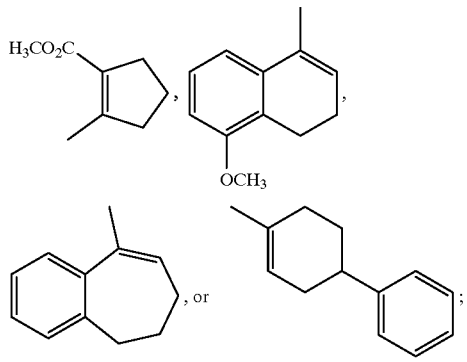
, or ;

R³ is hydrogen, straight chain alkyl of 1 to 6 carbon atoms optionally substituted with one COOR⁵, branched chain alkyl of 3 to 7 carbon atoms, cycloalkyl of 3 to 7 carbon atoms, or phenylalkyl of 7 to 12 carbon atoms optionally substituted with one COOR⁵, phenyl, or acyl group; and R⁴ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

comprising the steps:

a) attaching an R⁴ substituted 3-amino-4-iodo-benzoic acid of the formula

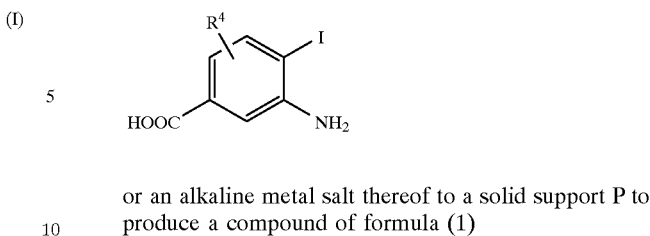

or an alkaline metal salt thereof to a solid support P to produce a compound of formula (1)

(1)

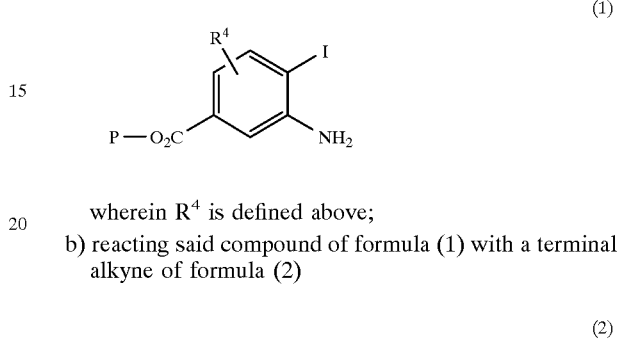

wherein R⁴ is defined above;

b) reacting said compound of formula (1) with a terminal alkyne of formula (2)

(2)

H≡≡R¹ wherein R¹ is defined above;
in the presence of a homogenous palladium(O) or palladium (II) catalyst and a secondary or tertiary amine base in a polar aprotic solvent at ambient temperature to produce a compound of formula (3)

(3)

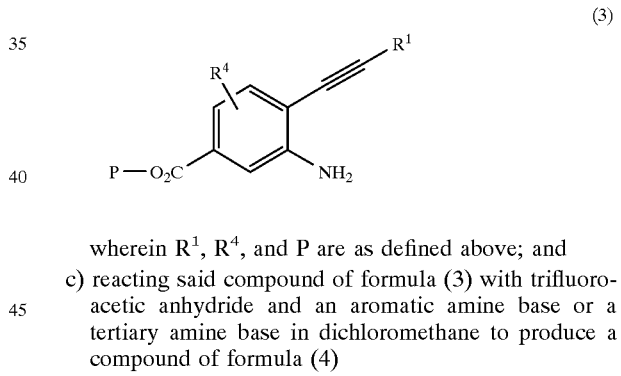

wherein R¹, R⁴, and P are as defined above; and c) reacting said compound of formula (3) with trifluoroacetic anhydride and an aromatic amine base or a tertiary amine base in dichloromethane to produce a compound of formula (4)

(4)

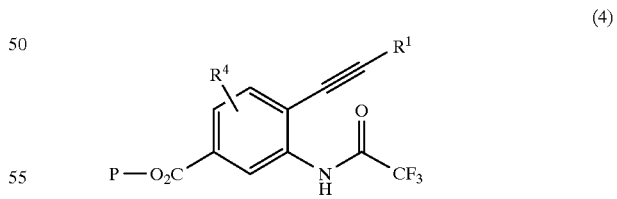

wherein R¹, R⁴, and P are as defined above; and d) reacting said compound of formula (4) with a vinyl trifluoromethanesulfonate of formula (5)

TfO—R² (5)

wherein R² defined above;
in the presence of a homogenous palladium(O) or palladium (II) catalyst and an inorganic base in a polar aprotic solvent to produce a compound of formula (6)

(6)

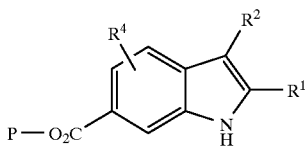

wherein $R^1$, $R^2$, $R^4$, and P are as defined above;

e) reacting said compound of formula (6) with an alkylating agent $R^3X$, where X is a suitable leaving group and $R^3$ is straight chain alkyl of 1 to 6 carbon atoms optionally substituted with one $COOR^5$ group where $R^5$ is hydrogen, straight chain alkyl of 1 to 6 carbon atoms, or phenylalkyl of 7 to 12 carbon atoms; branched chain alkyl of 3 to 7 carbon atoms, cycloalkyl of 3 to 7 carbon atoms, or phenylalkyl of 7 to 12 carbon atoms optionally substituted with one $COOR^5$ group, phenyl, or acyl group, in the presence of an alkaline metal or alkaline earth hydride in a polar aprotic solvent to produce a compound of formula (7)

(7)

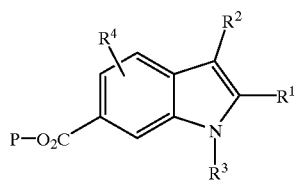

wherein $R^1$, $R^2$, $R^3$, $R^4$, and P are as defined above; and f) reacting said compound of formula (7) with a cleaving reagent to produce a compound of formula (I)

(I)

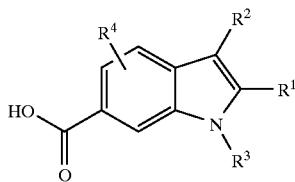

wherein $R^1$, $R^2$, $R^3$, and $R^4$ are as defined above.

7. The method of claim 1 wherein the palladium(O) catalyst is tetrakis (triphenylphosphine) palladium(O).

8. The method of claim 1 wherein the palladium(II) catalyst is bis(triphenylphosphine) palladium(II) chloride, copper (I) iodide.

9. The method of claim 1 wherein the secondary amine base is diethylamine.

10. The method of claim 1 wherein the tertiary amine base is triethylamine.

11. The method of claim 1 wherein the aromatic amine base is pyridine.

12. The method of claim 1 wherein the inorganic base is selected from the group consisting of potassium carbonate and sodium carbonate.

13. The method of claim 6 wherein the alkaline earth hydride is sodium hydride.

14. The method of claim 1 wherein the cleaving reagent is trifluoroacetic acid.

15. The method of claim 6 wherein the cleaving reagent is trifluoroacetic acid.

16. The method of claim 6 wherein the palladium(O) catalyst is tetrakis (triphenylphosphine) palladium(O).

17. The method of claim 6 wherein the palladium(II) catalyst is bis(triphenylphosphine) palladium(II) chloride, copper (I) iodide.

18. The method of claim 6 wherein the secondary amine base is diethylamine.

19. The method of claim 6 wherein the tertiary amine base is triethylamine.

20. The method of claim 6 wherein the aromatic amine base is pyridine.

21. The method of claim 6 wherein the inorganic base is selected from the group consisting of potassium carbonate and sodium carbonate.

22. The method of claim 6 wherein the solid support used is polystyrene crosslinked with divinylbenzene and functionalized with a linker group.

* * * * *